United States Patent [19]

Zimmerschied

[11] 4,111,986

[45] Sep. 5, 1978

[54] BUTANE OXIDATION TO ACETIC ACID

[75] Inventor: Wilford J. Zimmerschied, Naperville, Ill.

[73] Assignee: Standard Oil Company (Indiana), Chicago, Ill.

[21] Appl. No.: 788,984

[22] Filed: Apr. 19, 1977

[51] Int. Cl.² ............................................. C07C 51/20
[52] U.S. Cl. .............................. 562/549; 260/597 R; 560/241
[58] Field of Search .................................... 260/533 R

[56] References Cited

U.S. PATENT DOCUMENTS 3,247,249 4/1966 Saffer et al. ..................... 260/533 R Primary Examiner—Vivian Garner
Attorney, Agent, or Firm—William H. Magidson; Arthur G. Gilkes; William T. McClain

[57] ABSTRACT

Oxidizing butane to acetic acid which comprises contacting a sufficient concentration of an oxygen-containing gas with normal butane in the presence of catalyst consisting essentially of bromine and cobalt to initiate a self-sustaining exothermic reaction.

7 Claims, No Drawings

BUTANE OXIDATION TO ACETIC ACID

This invention relates to a process of oxidizing normal butane to acetic acid which comprises contacting a sufficient concentration of an oxygen containing gas with butane in the presence of a dissolved catalyst consisting essentially of bromine and cobalt to initiate a self-sustaining exothermic reaction. More particularly, this invention relates to a process of oxidizing normal butane to acetic acid which comprises injecting an oxygen containing gas below the surface of a reaction medium at a rate sufficient to initiate a self-sustaining exothermic reaction wherein said reaction medium comprises acetic acid solvent, butane and a dissolved catalyst consisting essentially of bromine and cobalt.

Numerous references describe metal/bromine catalyzed oxidation of organic compounds. For example, Olivier, U.S. Pat. No. 3,293,292, discloses a process of producing acetic acid by oxidizing normal butane using a catalyst comprising manganese, cobalt and bromine. The patentee indicates that each of the three components of the catalyst are essential in order to produce acetic acid. Example 1 of this patent describes a process which comprises charging an autoclave with acetic acid, cobalt acetate, manganese acetate and ammonium bromide, sealing the autoclave, adding normal butane to the solution, heating the reactants to about 350° F, pressurizing to 900 psig with nitrogen and then adding oxygen to the nitrogen blanket at a rate sufficient to maintain a pressure of about 930 psig. The reaction was considered to be terminated after two and a half hours when no further exotherm was observed. When this reaction was repeated in Example 6 except that the cobalt salt was omitted, no reaction occurred after one hour. Likewise, when this reaction was repeated in Example 6 except that the manganese salt was omitted, no oxidation occurred after one hour. Accordingly, Olivier considered that each metal component was essential.

Hay, U.S. Pat. No. 2,920,087, describes a process of preparing oxygenated products wherein oxygen is reacted with various organic compounds using a catalyst consisting essentially of cobalt, bromine and carboxylic acid wherein the ratio of bromine atoms to cobalt atoms is from 0.008 to 1.9. The patentee indicates at column 2, lines 67 to 70 that at higher bromine to cobalt atomic ratios, for example 2 to 1, the reaction terminates. At column 1, lines 55 et seq. Hay also indicates that the oxidation process should be carried out using no solvent or a suitable inert solvent having little water solubility and/or from which water can be rapidly removed by distillation. At column 4, lines 36 et seq. Hay indicates solvents in which water is appreciably soluble are generally unsatisfactory. Further, Hay points out that when appreciably water-soluble organic materials are oxidized, such as acetic acid, it is necessary to use inert solvents having little water solubility to effectively oxidize these compounds. Saffer et al U.S. Pat. No. 3,247,249 also discloses the liquid phase oxidation of various organic compounds using a metal/bromine catalyst.

The object of this invention is to provide a new process of producing acetic acid from butane. Other objects appear hereinafter.

We have now found that it is possible to produce acetic acid from normal butane in high yields by oxidizing butane using a dissolved catalyst consisting essentially of cobalt/bromine, provided sufficient oxygen is contacted with the butane to initiate a self-sustaining exothermic reaction. As explained below, it is preferred that gaseous oxygen is injected below the surface of the reaction medium at a rate sufficient to initiate a self-sustaining exothermic reaction. Contrary to the disclosure of Olivier, the process can be carried out with n-butane in the total absence of manganese provided the oxygen is injected below the surface of the reaction medium. If the oxygen is added to the air space above the reactants, as illustrated in Examples 1 and 6 of Olivier, there is substantially no reaction and manganese is an essential catalyst component. Accordingly, it is essential that the butane is contacted with sufficient oxygen, preferably by injection below the surface of the reaction medium, to initiate a self-sustaining exothermic reaction. Other things being equal, the omission of manganese in the instant process has the additional advantage that less propionic acid is formed during butane oxidation. Further, contrary to the disclosure of Hay, the bromine to cobalt atomic ratio can be more than 2 and the use of a water-soluble solvent, namely acetic acid, is advantageous since the acetic acid solvent does not constitute a by-product which must be separated from the desired oxidation product (acetic acid).

The solvent useful in this invention comprises acetic acid. Although the acetic acid can contain up to about 10% by weight water, it is preferred to employ glacial acetic acid since water has a somewhat inhibiting effect on the oxidation reaction. If desired various other substantially inert diluents such as benzene, can be used in conjunction with the acetic acid. As indicated above, acetic acid has the advantage that it does not constitute an undesirable by-product that must be separated from the main oxidation product. Various other organic acids can be employed. For example, recycled acetic acid from the butane oxidation can contain propionic acid, butyric acid, etc. The solvent (acetic acid and other diluents such as water, etc.) can constitute approximately 20 to 98 percent by weight of the reaction medium.

The catalyst useful in this invention consists essentially of a cobalt component and a bromine component. The ratio of monoatomic bromine component to cobalt can range from about 1:1 to 10:1 or higher, preferably 1.5 to 5:1. The catalyst components can be present in a concentration of about 1 to 50 millimole of cobalt and 2 to 500 milliequivalents of bromine per mole of butane. Tellurium, which is not a catalyst in this process, can be present in the reaction medium. As explained in commonly assigned application Ser. No. 788,731, filed on even date, the addition of tellurium permits the coproduction of acetic acid from butane and acetoxylation of $C_2$ or $C_3$ olefins to glycol acetates, since tellurium bromine catalyzes the acetoxylation reaction while the tellurium does not inhibit the butane oxidation.

Cobalt can be employed in any valence state such as the metal, divalent state or trivalent state. Suitable sources of cobalt include cobaltic bromide, cobaltous bromide, cobaltous or cobaltic salts of carboxylic acids containing from 1 to 18 carbon atoms, such as cobaltous formate, cobaltic acetate, cobaltic propionate, cobaltic stearate, cobaltic adipate, cobaltous succinate, etc. cobalt salts of mineral acids, such as cobaltic sulfate, cobaltous phosphate, cobaltic chloride, etc. In general, cobalt bromides and cobalt salts of acetic acid are preferred since the anion component of these catalysts do not introduce additional extraneous by-products into the reaction medium.

The bromine component of the catalyst can be added as elemental bromine, as a bromide ion, bonded to an organic group, etc. Suitable sources of bromine include bromine, hydrogen bromide, ammonium bromide, sodium bromide, potassium bromide, lithium bromide, cobaltous bromide, cobaltic bromide, tetrabromoethane, etc.

The oxygen containing gases useful in this invention can include air, substantially pure oxygen which can contain some argon, etc. Sufficient oxygen in the oxygen containing gas must be contacted with butane in the presence of dissolved catalyst to initiate a self-sustaining exothermic reaction. This can be accomplished by one of two techniques such as by turbulently mixing the oxygen and butane or by injecting the oxygen below the surface of the reaction medium. In either case each 100 grams of butane must be contacted with oxygen at a rate of at least 5 liters (S.T.P.) of oxygen per hour. If a lower rate than 5 liters of oxygen per hour are initially contacted with each 100 grams of butane, there is substantially no self-sustaining exothermic reaction. In order to assure the necessary contact and concentration of oxygen, the oxygen containing gas is preferably injected below the surface of the reaction medium. Even in this case, if the oxygen containing gas is bubbled into the reaction medium at a relatively slow rate (less than 5 liters of oxygen per hour per each 100 grams of butane) there is substantially no oxidation of the butane. The minimum concentration of oxygen necessary to initiate a self-sustaining exothermic reaction is dependent in part on the catalyst components. For example, other things being equal, oxygen must be injected at a substantially higher rate (about 3 times the rate) to initiate a self-sustaining exothermic reaction using a cobaltous acetate/ammonium bromide catalyst system instead of cobaltous bromide. The optimum rate of injection of the oxygen containing gas can be determined by routine experimentation. In general, it is preferred to inject the oxygen containing gas at a rate of at least 10 liters of oxygen per hour per each 100 grams of butane. After the self-sustaining reaction becomes exothermic, the rate of oxygen addition can be and advantageously is increased many fold. On a batch basis, utilizing the preferred technique, the reaction typically takes approximately 30 minutes to 2 hours to completely oxidize 150 grams of butane in 250 grams acetic acid. If desired, the oxygen containing gas and butane can be premixed and added, preferably injected, together into the reaction medium. However, if this technique is employed, the concentration of the oxygen containing gas and butane should be adjusted to be outside of the explosive limits to minimize safety hazards.

The oxidation can be carried out at a temperature of about 150° to 450° F. Butane is preferably oxidized at a temperature of at least 350° F. Other things being equal, as the reaction temperature increases from 300° to 350° F the initiation time for the reaction decreases from 4½ to 1½ minutes and the product yield increases. The lower yield at lower temperatures is apparently due to partial deactivation of the catalyst by water produced in the reaction.

Although the reaction is generally controlled by the concentration of oxygen injected into the reaction medium, the maximum conversion of butane is limited by the catalyst concentration when the catalyst concentration drops below 3 milliequivalents of cobalt or 7 milliequivalents of bromine per mole of butane. Above this level, the oxygen concentration determines the yield of product.

The process can be carried out at a pressure of about 500 to 3000 psig preferably about 800 to 1500 psig. However, the pressure is relatively unimportant provided oxygen is injected below the surface of the reaction mixture at a rate sufficient to produce an exothermic reaction.

The oxidation can be conducted on a batch or continuous basis. In either case, the solvent, butane, cobalt and bromine compounds are, in general, charged to the reactor and heated to the reaction temperature. The oxygen containing gas is thereafter preferably injected below the surface of the reaction medium at a rate sufficient to initiate self-sustaining exothermic reaction cleaving each molecule of butane into approximately two molecules of acetic acid in a stepwise process which apparently proceeds through the formation of methyl ethyl ketone and diacetyl. As indicated above, the oxidation is complete when no exothermic reaction occurs at a rapid rate of oxygen addition.

The oxidation product can be purified by fractional distillation of low boiling ester fractions such as methyl acetate, ethyl acetate, etc. and the acetic acid recovered in the heart cut. For some purposes purification of the acetic acid is unnecessary other than the removal of the low boilers. For example, acetic acid contaminated with some bromine containing residues can be used as a solvent medium for the oxidation of paraxylene or metaxylene to terephthalic acid and isophthalic acid since the bromine/cobalt catalyst system is commercially employed to produce these aromatic acids. Likewise acetic acid contaminated with some bromine containing residues, propionic acid and butyric acid can be cycled as the solvent medium for oxidation of butane. The various lower boiling esters can be hydrolyzed and the acetic acid recovered by conventional techniques or they can be recycled to the solvent medium for further oxidation.

In a continuous process, the partially oxidized butane is preferably backmixed in order to completely oxidize butane to acetic acid. Failure to backmix generally results in the final product containing both methyl-ethyl ketone and diacetyl.

EXAMPLE I

A 1 liter titanium autoclave equipped with a magnetic drive, cooling coil, dip-leg, thermocouple, vent, knockback condensor and Ruska pump, containing 5 moles glacial acetic acid and 17 millimoles of cobaltous bromide hexahydrate was sealed and pressurized to 200 to 250 psig with nitrogen. After 2.5 moles of liquid butane was charged to the reactor using the Ruska pump, the reactor was pressurized to 400 to 500 psig with nitrogen and heated to 350° F. After the pressure was increased to 850 psig with nitrogen, the heat was turned off, and oxygen added through the dip-leg at a rate of 34 liters (STP) per hour per each 100 grams of butane in the reactor. The reaction became exothermic after 1½ minutes and the oxygen flow was increased to 97 liters of oxygen per hour per each 100 grams of butane. After 70 minutes the exothermic reaction was terminated. The product weighed 185 percent of the weight of the starting acetic acid and catalyst charged to the reactor and comprised 81.4% by weight acetic acid, 0.79 wt.% propionic acid, and 10.7% by weight water indicating that there was conversion of approximately 71 mole percent of butane charged to acetic acid. Based on butane converted, the selectivity to acetic acid was 77.5%.

EXAMPLE II

Example I was repeated except that the catalyst was 7 millimoles of cobaltous acetate and 18.4 millimoles of ammonium bromide and the reaction temperature was initiated at 300° F. In this case the initiation time was 4.5 minutes and the liquid product weighed 159 percent of the starting weight of catalyst and acetic acid in the reactor and comprised 83.2% by weight acetic acid and 9.46% water.

EXAMPLE III

Example I was repeated except that the catalyst was 7 millimoles of cobaltous acetate and 18.4 millimoles of ammonium bromide and the reaction was initiated at 355° F. After 47 minutes the oxygen addition was terminated with a product yield of 152 percent based on the starting weight of acetic acid and catalyst and comprised 84.5% by weight acetic acid and 8.93% water.

EXAMPLE IV

This example illustrates that oxygen must be injected below the level of the acetic acid reaction medium. Example III was repeated except that the knock back condensor was removed, the oxygen was added to the nitrogen blanket above the liquid level of the reaction medium and the reaction temperature was maintained at 350° F. A total of 40 psig oxygen was added to raise the pressure of the reactor to 940 psig. After 60 minutes at 350° F there was no reaction. Accordingly, this example illustrates that oxygen must be injected below the level of the reaction medium.

When this example was repeated using 7 millimoles cobaltous acetate and 70 millimoles of ammonium bromide and 30 psig of oxygen was charged to the nitrogen blanket to pressurize the reactor to 930 psig, there was no reaction after 60 minutes at 350° F.

EXAMPLE V

This example illustrates that acetic acid can be produced by adding oxygen to the nitrogen blanket provided that the catalyst contains a manganese component as indicated in the aforesaid Olivier patent. Example II was repeated except that the catalyst comprised 7.3 millimoles of manganese acetate in addition to the cobaltous acetate and ammonium bromide utilized in Example II and oxygen was added to the nitrogen blanket. Oxygen was added until the pressure in the reactor reached 940 psig. and then addition was terminated. After one hour the pressure had increased to 970 psig but no exotherm was observed. The pressure was reduced to 900 psig by venting, and oxygen was again added. The reaction exothermed 110 minutes after the initial addition of oxygen and the run was terminated after 151 minutes. Product yield was 156 weight percent based on starting catalyst and acetic acid and comprised 83.7% by weight acetic acid, 2.92% by weight propionic acid and 10.3% water.

EXAMPLE VI

This example illustrates that oxygen must be injected below the level of acetic acid reaction medium. The technique described in the first paragraph of Example IV was repeated using a 2 hour reaction time instead of 60 minutes. In this case oxygen was charged to the nitrogen blanket to raise the pressure from 900 to 930 psig. 25 minutes after the start of the reaction some heat of reaction was observed but it ceased and then restarted 56 minutes after the start of the reaction. The remainder of the run was carried out at 970 psig with intermittent reactions apparently taking place. A product yield of 119 percent based on the starting weight of acetic acid and catalyst was obtained.

When the process described in the preceding paragraph was repeated there was no reaction after 50 minutes had elapsed. After the pressure was reduced from 970 to 900 psig by venting, an additional 60 psig of oxygen was added to the nitrogen blanket producing a very slight reaction. A product yield of 111 percent based on the starting weight of acetic acid and catalyst was obtained.

The above runs illustrate that oxygen must be injected below the level of acetic acid reaction medium in order to obtain an exothermic reaction and meaningful yields.

EXAMPLE VII

This example illustrates a method of determining the minimum oxygen rate necessary to initiate a self-sustaining exothermic reaction utilizing cobaltous bromide, a preferred catalyst. Generally, the technique described in Example I was as follows:

(a) Into a 1-liter titanium magne-drive autoclave fitted with a knock-back condenser was charged 300 grams (5.0 moles) of acetic acid and 2.29 grams (7 millimoles) of cobaltous bromide hexahydrate. The reactor was pressured to 200 psig with nitrogen, and then 2.5 moles of n-butane was fed into the reactor by means of a Ruska pump. Stirring was started and the reactor was heated to 350° F. Additional nitrogen was then added to the reactor so that the pressure reached 860 psig. Oxygen was added through a dip-leg the end of which was within one-half inch of the bottom of the reactor at a rate of 0.132 ft$^3$/hour (corresponds to 2.6 liters/hour STP) per 100 grams of butane. After 27 minutes the reactor pressure reached 900 psig without any evidence of an exotherm. At time, 30 minutes, the run was terminated.

(b) Paragraph (a) was repeated except that after reaching a reactor pressure of 860 psig, oxygen was added at a rate of 0.238 ft$^3$ per hour (corresponds to 4.6 liters/hour at STP) per 100 grams of butane. During the 33 minutes it took to reach 900 psig, there were two very slight exotherms, one at 7 minutes and one at 18 minutes. Each time the reaction died out. Accordingly, with this catalyst system, more than 4.6 liters per hour of oxygen per 100 grams of butane are required to initiate a self-sustaining exothermic reaction.

(c) The process of paragraph (a) was repeated except that after reaching a pressure of 860 psig, oxygen was added at a rate of 0.326 ft$^3$ per hour (corresponding to 6.4 liters/hour STP) per 100 grams of butane. After 6½ minutes an exothermic self-sustaining reaction occurred as evidenced by a temperature rise. Reactor pressure at the time of initiation was about 870 psig.

(d) When the process of Paragraph (a) was repeated except that after reaching a pressure of 860 psig oxygen was added at a rate of 1.672 ft$^3$ per hour (corresponding to a rate of 32.6 liters/hour STP) per 100 grams butane, a self-sustaining exothermic reaction was initiated after 1 minute.

The above data illustrates that a self-sustaining exothermic reaction could be initiated by adding between 4.6 liters and 6.4 liters per hour of oxygen per 100 grams of butane and that the induction period is dependent upon the rate of addition of oxygen. The faster the rate of oxygen addition the shorter the induction period.

EXAMPLE VIII

This example illustrates the continuous production of acetic acid. Into a 1-liter titanium Magne-Drive autoclave fitted with a knock-back condenser, dip legs for butane and oxygen addition, a cooling coil and a liquid level control which operated a research control valve to maintain the liquid level in the reactor were charged 300 grams (5.0 moles) of acetic acid and 2.29 grams (7 mmoles) of CoBr$_2$.6H$_2$O. The reactor was pressured to 200 psig, and 2.5 moles of liquid butane was charged. The reactor was heated to 350° F and the heaters turned off. It was then pressured to 860 psig with nitrogen. Oxygen was added and after the reaction initiated, butane and catalyst (CoBr$_2$.6H$_2$O dissolved in acetic acid) were pumped into the reactor. Summary of data is in Tables A and B.

TABLE A

| Operating Data For The Continous Oxidation Of Butane | |
|---|---|
| Feed Rates | |
| Butane, Moles/Hr. | 2.40 |
| Catalyst | |
| CoBr$_2$.6H$_2$O mmoles/Hr. | 16.8 |
| Acetic Acid, Moles/Hr. | 0.63 |
| Oxygen, Moles/Hr. | 8.23 |
| Run Conditions | |
| Residence Time, Hrs. | 0.77 |
| Reactor Pressure, psig | 900 |
| Temperature, ° F | 355 |
| Vent Gas Oxygen, % | ca. 5 |
| Time For Lining out, Hrs. | 3.0 |
| Time For Product, Hrs. | 2.0 |
| Liquid Product, wt. gr. | 587.7 |

TABLE B

| Selectivity Data For Continuous Butane Oxidation Run | |
|---|---|
| Butane Charged = | 4.80 moles |
| Butane Recovered = | 0.85 moles |
| Butane Consumed = | 3.95 moles |
| Butane Accountability = 90% | |
| Indicated Conversion = 82.3% | |

| | Product Selectivity | | | |
|---|---|---|---|---|
| Compound | Moles | Moles Butane, Equivalent | Mole % Selectivity Based On Butane Converted | (1) |
| Formic Acid | 0.025 | 0.0063 | 0.16 | (0.18) |
| Methyl Acetate | 0.126 | 0.095 | 2.39 | (2.68) |
| Ethyl Acetate | 0.068 | 0.068 | 1.73 | (1.92) |
| Methyl Ethyl Ketone | 0.113 | 0.113 | 2.84 | (3.18) |
| Propionic Acid | 0.110 | 0.082 | 2.07 | (2.31) |
| Butyric Acid | 0.036 | 0.036 | 0.90 | (0.10) |
| CO$_2$ + CO | 1.54 | 0.385 | 9.73 | (10.9) |
| Acetic Acid | 5.53 | 2.77 | 70.1 | (78.0) |

(1) Assumed that missing 10.0% butane is unreacted. Butane conversion is 74%.

I claim:

1. The process of oxidizing butane to acetic acid which comprises contacting a sufficient concentration of an oxygen-containing gas with normal liquid butane in the presence of a dissolved catalyst consisting essentially of bromine and cobalt in a solvent medium comprising acetic acid to initiate a self-sustaining exothermic reaction, wherein each 100 grams of butane is contacted with oxygen at a rate of at least 5 liters of oxygen per hour.

2. The process of claim 1 wherein an oxygen containing gas is injected below the surface of the reaction medium at a rate sufficient to initiate a self-sustaining exothermic reaction.

3. The process of claim 2 wherein the catalyst components are present in a concentration of from about 1 to 50 milliequivalents of cobalt and 2 to 500 milliequivalents of bromine per mole of butane.

4. The process of claim 3 wherein said catalyst is cobaltous bromide.

5. The process of claim 1 wherein each 100 grams of butane is contacted with oxygen at a rate of at least 10 liters of oxygen per hour to initiate said self-sustaining exothermic reaction.

6. The process of claim 5 wherein an oxygen-containing gas is injected below the surface of the reaction medium at a rate sufficient to initiate a self-sustaining exothermic reaction.

7. The process of claim 6 wherein the catalyst components are present in a concentration of from about 1 to 50 milliequivalents of cobalt and 2 to 500 milliequivalents of bromine per mole of butane.

* * * * *